United States Patent
Robertson et al.

(10) Patent No.: US 7,284,604 B2
(45) Date of Patent: Oct. 23, 2007

(54) METHODS FOR MEASUREMENT OF A DIMENSIONAL CHARACTERISTIC AND METHODS OF PREDICTIVE MODELING RELATED THERETO

(75) Inventors: Eric P Robertson, Idaho Falls, ID (US); Richard L. Christiansen, Littleton, CO (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 11/737,061

(22) Filed: Apr. 18, 2007

(65) Prior Publication Data

US 2007/0193742 A1    Aug. 23, 2007

Related U.S. Application Data

(62) Division of application No. 10/835,761, filed on Apr. 29, 2004, now Pat. No. 7,224,475.

(51) Int. Cl.
*E21B 49/00* (2006.01)
*E21B 43/25* (2006.01)

(52) U.S. Cl. ............. 166/250.02; 73/865.6; 73/866; 166/250.01; 166/305.1; 356/244; 356/625; 356/634; 405/129.35; 703/10

(58) Field of Classification Search ........... 166/250.02; 703/10
See application file for complete search history.

(56) References Cited

U.S. PATENT DOCUMENTS

| | | | |
|---|---|---|---|
| 2,623,596 A * | 12/1952 | Dyes et al. ............ 166/402 |
| 3,384,416 A | 5/1968 | Ruehl | |
| 3,421,819 A | 1/1969 | Anderson et al. | |
| 4,014,214 A | 3/1977 | Pontefract | |
| 4,083,228 A | 4/1978 | Turner et al. | |
| 4,083,395 A | 4/1978 | Romano | |
| 4,369,652 A | 1/1983 | Gundlach | |
| 4,372,652 A | 2/1983 | Pontefract | |
| 4,408,489 A | 10/1983 | Spangle | |
| 4,561,305 A | 12/1985 | Tremain et al. | |
| 4,653,331 A | 3/1987 | Inouye et al. | |
| 4,885,941 A | 12/1989 | Vardoulakis et al. | |

(Continued)

OTHER PUBLICATIONS

Reucroft et al., "Gas-induced swelling in coal," Fuel, 1986, vol. 65, Jun. pp. 816-820.

(Continued)

*Primary Examiner*—George Suchfield
(74) *Attorney, Agent, or Firm*—Trask Britt

(57) ABSTRACT

A method of optically determining a change in magnitude of at least one dimensional characteristic of a sample in response to a selected chamber environment. A magnitude of at least one dimension of the at least one sample may be optically determined subsequent to altering the at least one environmental condition within the chamber. A maximum change in dimension of the at least one sample may be predicted. A dimensional measurement apparatus for indicating a change in at least one dimension of at least one sample. The dimensional measurement apparatus may include a housing with a chamber configured for accommodating pressure changes and an optical perception device for measuring a dimension of at least one sample disposed in the chamber. Methods of simulating injection of a gas into a subterranean formation, injecting gas into a subterranean formation, and producing methane from a coal bed are also disclosed.

5 Claims, 6 Drawing Sheets

U.S. PATENT DOCUMENTS

| | | |
|---|---|---|
| 4,923,307 A | 5/1990 | Gilmore et al. |
| 4,924,695 A | 5/1990 | Kolpak |
| 4,976,549 A | 12/1990 | Khan |
| 5,082,635 A | 1/1992 | Wakatsuki et al. |
| 5,170,366 A | 12/1992 | Passarelli |
| 5,172,977 A | 12/1992 | Enustun et al. |
| 5,248,200 A | 9/1993 | Walsh |
| 5,606,132 A | 2/1997 | Simpson |
| 5,710,726 A * | 1/1998 | Rowney et al. ............... 703/10 |
| 5,844,684 A | 12/1998 | Maris et al. |
| 5,877,426 A | 3/1999 | Hay et al. |
| 6,019,841 A | 2/2000 | Jafri et al. |
| 6,082,174 A | 7/2000 | Lee et al. |
| 6,108,608 A * | 8/2000 | Watts, III ................... 702/30 |
| 6,476,922 B2 | 11/2002 | Paganelli |
| 6,527,438 B2 | 3/2003 | Zollinger et al. |
| 6,591,690 B1 | 7/2003 | Crockford |
| 6,618,677 B1 * | 9/2003 | Brown ........................ 702/13 |
| 6,981,549 B2 * | 1/2006 | Morales et al. .......... 166/250.1 |
| 7,006,959 B1 * | 2/2006 | Huh et al. .................... 703/10 |
| 2001/0045291 A1 * | 11/2001 | Mones ....................... 166/400 |
| 2003/0108082 A1 | 6/2003 | Paganelli |
| 2006/0180306 A1 * | 8/2006 | Stone ....................... 166/252.6 |

OTHER PUBLICATIONS

Sagüés, A.A., "Dilatometer for the in situ observation of high-temperature, high-pressure hydrogen attack," Rev. Sci. Instrum., 50(1), Jan. 1979, pp. 48-51.

* cited by examiner

Optically measuring dimensional changes of a coal composition as a function of exposure to a selected gas over a range of pressure Relating the optically measured dimensional changes of the coal composition to a permeability characteristic thereto Simulating injection of the selected gas into a subterranean formation including the coal composition

METHODS FOR MEASUREMENT OF A DIMENSIONAL CHARACTERISTIC AND METHODS OF PREDICTIVE MODELING RELATED THERETO

CROSS-REFERENCE TO RELATED APPLICATIONS

This Application is a Divisional of U.S. application Ser. No. 10/835,761 entitled METHODS AND APPARATUS FOR MEASUREMENT OF A DIMENSIONAL CHARACTERISTIC AND METHODS OF PREDICTIVE MODELING RELATED THERETO, filed on Apr. 29, 2004 now U.S. Pat. No. 7,224,475.

GOVERNMENT RIGHTS

The United States Government has rights in the following invention pursuant to Contract No. DE-AC07-99ID13727 and Contract No. DE-AC07-05ID14517 between the U.S. Department of Energy and Battelle Energy Alliance, LLC.

BACKGROUND OF THE INVENTION

1. Field of the Invention

The present invention relates generally to methods and systems for measuring a dimensional change of a material in response to a change in environment. Particularly, the methods and apparatus of the present invention relate to measuring a dimensional change of coal in response to exposure to a gas, such as, for instance, carbon dioxide at a selected pressure.

2. State of the Art

Subterranean coal seams may contain substantial quantities of natural gas, primarily in the form of methane. The methane may be contained within the coal as adsorbed gas and various techniques have been developed to enhance removal of the methane therefrom. However, the rate of recovery of methane from coal seams may typically depend on the rate at which gas can flow through the coal seam to a production well. The flow rate of methane through a coal seam may be affected by many factors including, for instance, the porosity of the coal, the permeability of the coal, the extent, if any, of the fracture system which exists within the coal seam, and the stress therein.

Typically, the naturally occurring system of fractures within a coal seam does not provide for an acceptable methane recovery rate. Therefore, in general, coal seams must be stimulated to enhance the recovery of methane from the seams. Techniques for increasing the methane production rate often attempt to increase the permeability of the coal, which will permit an increase in the rate of production of methane from the coal seam.

For instance, one technique for stimulating the coal formation in the near wellbore region involves the fracturing of the coal bed by injecting under substantial pressure an aqueous mixture with suitable entrained particles as propping agents to open up fracture planes and channels in which the particles settle out to prop the fractures open as they are formed. Such entrained particles are commonly termed "proppants," which may comprise sand grains, man-made or specially engineered proppants, resin-coated sand, or ceramic materials. Although hydraulic fracturing of coal seams may be effective in increasing the permeability of the coal, fracturing fluids may cause, in the long term, a loss in methane productivity due to adsorption of the fracturing fluids onto the coal fracture surfaces. Adsorption of the fluid may cause swelling of the coal itself, which may plug the coal cleat or natural fracture system and inhibit recovery of methane therefrom.

Another technique to stimulate coal bed methane production from a coal seam is to inject a gas, such as air, nitrogen, ammonia, or carbon dioxide, into the coal seam. This process may be commonly referred to as "enhanced coal bed methane (ECBM) production." This technique has been utilized in the past to degasify coal mines for safety reasons. For instance, U.S. Pat. No. 3,384,416 discloses such a technique where a refrigerant fluid with proppants is injected into the coal seam to fracture the coal. The injected refrigerant fluid and methane may escape from a borehole drilled into the coal under its own pressure or the injected refrigerant fluid and methane may be removed via pumps.

U.S. Pat. No. 4,083,395 discloses a technique for recovering methane from a coal seam where a carbon dioxide-containing fluid is introduced into the coal deposit through an injection well and held therein for a period sufficient to enable a substantial amount of methane to be desorbed from the surfaces of the coal deposit. Following the so-called hold period, the injected carbon dioxide-containing fluid and desorbed methane may be recovered through a recovery well or wells spaced from the injection well. The process is repeated until sufficient methane has been removed to enable safe mining of the coal deposit.

Of course, there must be at least one injection well and at least one production well for the enhanced in situ degasification of coal deposits. More preferably, a suitable plurality of injection wells and a plurality of gas production wells may be formed within the coal deposit. The position of the plurality of injection wells and the plurality of gas production wells may be selected for maximum economy in recovery of the methane contained therein.

In addition, besides being reservoirs for methane, coal beds have enormous carbon dioxide storage potential. Therefore, in addition to any methane that may be produced from a coal bed, coal beds have been considered as a storage mechanism for retaining carbon dioxide gas. Such carbon dioxide sequestration may be employed for storing carbon dioxide produced as a by-product of industry or as otherwise may be desirable.

However, pertaining to either methane production or carbon dioxide sequestration, it has been found that injection of gasses may cause the coal to swell, which may reduce the permeability of the coal. Of course, coal swelling may also affect the stress state of the coal and may further affect the permeability of the coal. Further, and as mentioned above, the permeability of the coal may influence methane production from a coal bed or carbon dioxide sequestration within a coal bed.

The swelling or expansion of certain coals as a function of elevated temperature is a well-known and studied characteristic. This swelling behavior, also referred to as dilation, may be related, although not precisely, to the volatility of the coal. However, the suitability of any particular coal for gas production may be more accurately determined from knowledge of the actual swelling characteristics of the coal, rather than from the volatile matter content of the coal, since the swelling property may be a characteristic more precisely related to changes in permeability.

A conventional apparatus for measuring the temperature dependent swelling behavior (i.e., coefficient of thermal expansion) of materials is a dilatometer. One example of a conventional dilatometer is disclosed in U.S. Pat. No. 4,923,307 to Gilmore et al. Additionally, modified conventional dilatometers have been used for measuring dimensional changes in other materials, and sometimes under controlled conditions. For instance, an article, published in Rev. Sci. Instrum., 1979, and titled DILATOMETER FOR THE IN SITU OBSERVATION OF HIGH-TEMPERATURE HIGH-PRESSURE HYDROGEN ATTACK by A. A. Sagüés describes a test apparatus comprising an autoclave within which a sample and a control sample may be disposed. The autoclave chamber may be heated, and hydrogen may be introduced thereinto. Also, disposed within the autoclave chamber is a capacitive displacement sensor, which indicates the relative expansion of the sample. Electrical signals from the sensor are carried through the wall of the autoclave chamber via an electrical feedthrough.

Other examples of modified dilatometers may be found in U.S. Pat. No. 6,476,922 and U.S. patent application Ser. No. 10/293,342, both to Pananelli. Both U.S. Pat. No. 6,476,922 and U.S. patent application Ser. No. 10/293,342 relate to a dilatometer including at least two optical systems which are able to focalize, with a predetermined degree of magnification, the images of two ends of the test piece. The apparatuses are structured to perform measurement of a size of a test piece while completely eliminating any influence on such measurement by the holder or the measuring system.

Unfortunately, however, while a number of authors have proposed models that attempt to relate coal swelling characteristics to permeability changes, the inventors of the present invention are aware of very little data published on the swelling properties of coal under different gas environments which is available for incorporation into mathematical models. More particularly, if the relationship between swelling or shrinkage of coal in relationship to different gases and pressures were more easily determined experimentally, mathematical modeling of the injection process, for either methane production or carbon dioxide sequestration, may be improved. Furthermore, the injection process itself may correspondingly benefit by way of more accurate predictive models thereof.

One conventional approach for measuring the swelling characteristics of coal under different gas environments is to utilize one or more strain gages affixed to the surface of a coal sample. Such a conventional procedure requires affixing a strain gage adhesively to the surface of a coal sample. It has been noted that the conventional adsorption or desorption process may be extremely slow, taking nearly three months for the coal matrix strains to stabilize. As a further note, a strain gauge may have an elasticity that is not negligible with respect to the elasticity of the coal sample to which it is affixed, and thus may introduce artifact (i.e., extraneousness or inaccuracy) into the strain gauge reading.

In view of the foregoing problems and shortcomings with existing apparatus, methods, and systems for testing and modeling the dimensional behavior of permeable materials such as coal, as well as the need for data useful for modeling such materials, it may be desirable to provide improved methods and apparatus for determining the dimensional behavior of permeable materials, particularly as related to pressurized gas environments.

BRIEF SUMMARY OF THE INVENTION

The present invention relates to a method of optically indicating a dimensional characteristic of a sample in response to a selected change in environment. Further, at least one sample may be disposed within a chamber and at least one environmental condition within the chamber may be altered. Then, at least one dimension of the at least one sample subsequent to altering the at least one environmental condition within the chamber may be optically determined.

For instance, a coal sample may be placed within a chamber and carbon dioxide gas introduced to increase a magnitude of pressure within the chamber. A dimension of the coal sample may be measured subsequent to the increase in pressure within the chamber. Of course, other environmental conditions such as temperature and humidity may be monitored or controlled, or both monitored and controlled.

Further, a maximum change in dimension of the at least one sample in response to altering the at least one condition within the chamber may be predicted. Prediction of the maximum change in dimension of the at least one sample in response to altering the at least one condition within the chamber may occur by determining a best fit via experimentally obtained data with respect to the following mathematical relationship:

$$S_{FINAL}(\Delta P) = \frac{S(t) \cdot (T+t)}{t}.$$

Thus, predicting a maximum change in dimension may occur prior to the at least one dimension of the at least one sample equilibrating in relation to altering the at least one condition within the chamber.

The present invention also contemplates a dimensional measurement apparatus for indicating changes in at least one dimension of at least one sample. Specifically, the dimensional measurement apparatus may include a housing, such as a pressure vessel, comprising a chamber configured for accommodating variations in a pressure therein. Further, the dimensional measurement apparatus may also include an optical perception device for measuring a dimension of at least one sample disposed within the chamber.

A further facet of the present invention relates to a method of simulating injection of a gas into a subterranean formation comprising coal. In one aspect, dimensional changes of a particular coal composition may be measured in relation to exposure thereof to a selected gas over a range of pressure. Also, the optically measured dimensional changes of the coal composition may be related (i.e., mathematically, empirically, or otherwise) to a permeability characteristic of the coal composition. Further, injection of the selected gas into a subterranean formation including the coal composition may be simulated.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention relates to methods and apparatus for measuring a dimensional change in test samples of a selected material. For instance, the present invention relates to measurement of one or more dimensional changes in a material, such as, for instance, coal, in response to exposure to a change in an environmental condition, such as exposure to a particular gas at a selected magnitude of pressure.

Figure 1A:
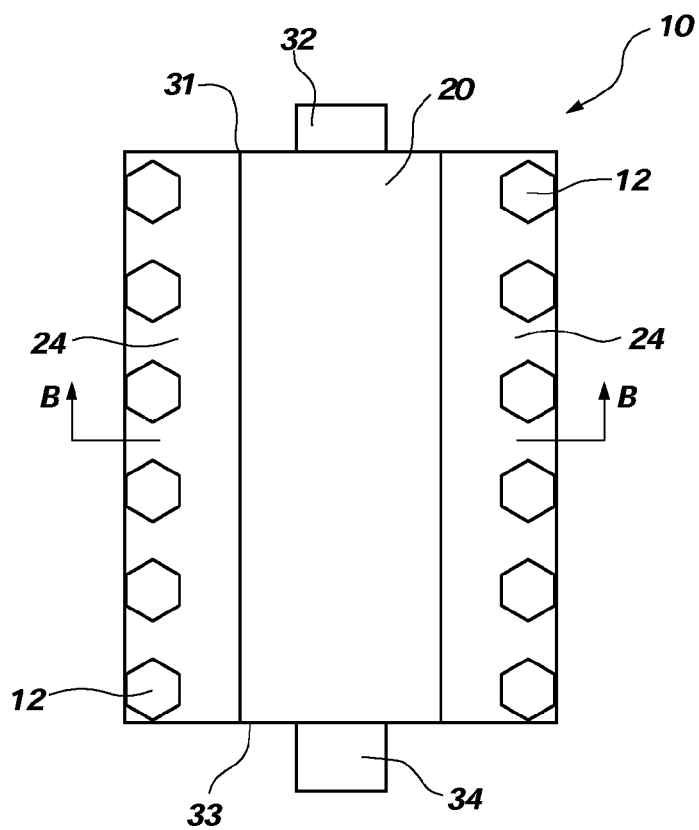
FIG. 1A shows a top elevation view of an exemplary pressure vessel in accordance with the present invention.
Figure 1B:
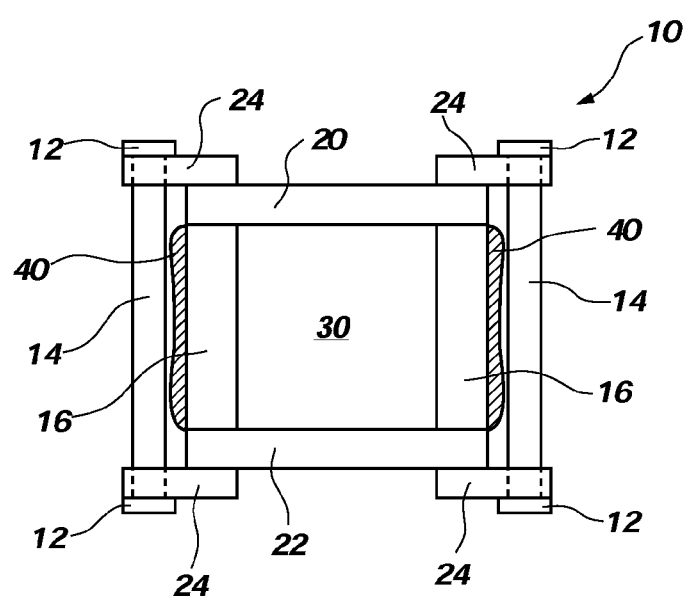
FIG. 1B shows a cross-sectional view of the pressure vessel shown in FIG. 1A taken across line B-B.

FIGS. 1A and 1B show a top elevation view of an exemplary housing in the form of a pressure vessel 10 and a cross-sectional view along reference line B-B as shown in FIG. 1A of pressure vessel 10, respectively. Referring to FIGS. 1A and 1B, pressure vessel 10 forms closed chamber 30 between side walls 16, upper window 20, and lower window 22. Upper window 20 and lower window 22 may be compressed against side walls 16 by way of tensioning members 14 that extend between flange plates 24. Tensioning members 14 may each comprise a rod with threaded ends that each may extend through each of flange plates 24 and may be engaged by a threaded nut 12. Flange plates 24 may be sized and positioned to overlap with upper window 20 and lower window 22. Accordingly, threaded nuts 12 may be tightened, which may compress the upper window 20 and the lower window 22 against side walls 16. Of course, additional sealing mechanisms may be employed to seal between upper window 20 and side walls 16 and between lower window 22 and side walls 16. For instance, elastomeric sealing elements, such as gaskets or silicone sealing compounds may be employed to seal between upper window 20 and side walls 16 and between lower window 22 and side walls 16, respectively. In addition, ends 31 and 33 of pressure vessel 10 may be sealed by way of respective end caps (not shown), which may also include elastomeric sealing elements such as gaskets or silicone sealing compounds. Thus, chamber 30 may be configured for developing pressurized or even vacuum environments therein.

Upper window 20 and lower window 22 may each comprise a tempered glass, polycarbonate, or another substantially transparent, suitable material and may be sized to an appropriate thickness in relation to an expected magnitude of pressure, which may be greater than or less than ambient atmospheric pressure, within chamber 30. Upper window 20 and lower window 22 may allow for optical perception of objects within chamber 30. Particularly, positioning of upper window 20 and lower window 22 along the opposing sides of chamber 30 may facilitate viewing thereof by allowing light to pass into one of upper window 20 and lower window 22 and to pass out of chamber 30 from the other of upper window 20 and lower window 22. However, while two or more windows into chamber 30 may facilitate optical perception of objects disposed therein, multiple windows may not be desired. Therefore, more generally, the present invention contemplates that chamber 30 may include at least one window for optical perception of objects disposed therein, without limitation. One apparatus that may be used as a chamber 30 is a so-called Jerguson fluid level gauge or flat glass gauge, which is commercially available from Clark-Reliance Corporation of Strongsville, Ohio.

End 31 of pressure vessel 10 may comprise port 32, which maybe configured for introducing gas or other fluid to chamber 30. Also, end 33 of pressure vessel 10 may comprise port 34, which may be configured for removing gas or other fluid from chamber 30. Port 32 and port 34 may also be used for disposing thermocouples therethrough, or disposing other sensors, mechanical elements, or other desired components.

Thus, pressure vessel 10 may be configured for external optical viewing of the chamber 30 therein. Further, the chamber 30 may be configured for pressurization to a desired magnitude of pressure with a selected gas via ports 32 and 34. Optionally, other environmental aspects of the chamber 30 of the pressure vessel 10 may also be controlled. For instance, relative humidity, temperature, or both, may be controlled. Explaining further, the relative humidity of a gas passing into chamber 30 may be influenced prior to introduction thereinto. Also, heaters 40 may be disposed proximate to chamber 30, within chamber 30, or both, and may be configured, in combination with at least one temperature sensor (not shown), for controlling the temperature within chamber 30 as known in the art. For instance, heaters 40 may comprise a so-called heat tape, which includes at least one electrical resistance heating element. Further, a controller, such as a controller employing a so-called proportional-integral-derivative ("PID") algorithm may be utilized in conjunction with a thermocouple for controlling the temperature of the heat tape and thus, controlling the temperature of the chamber 30.

Figure 2A:
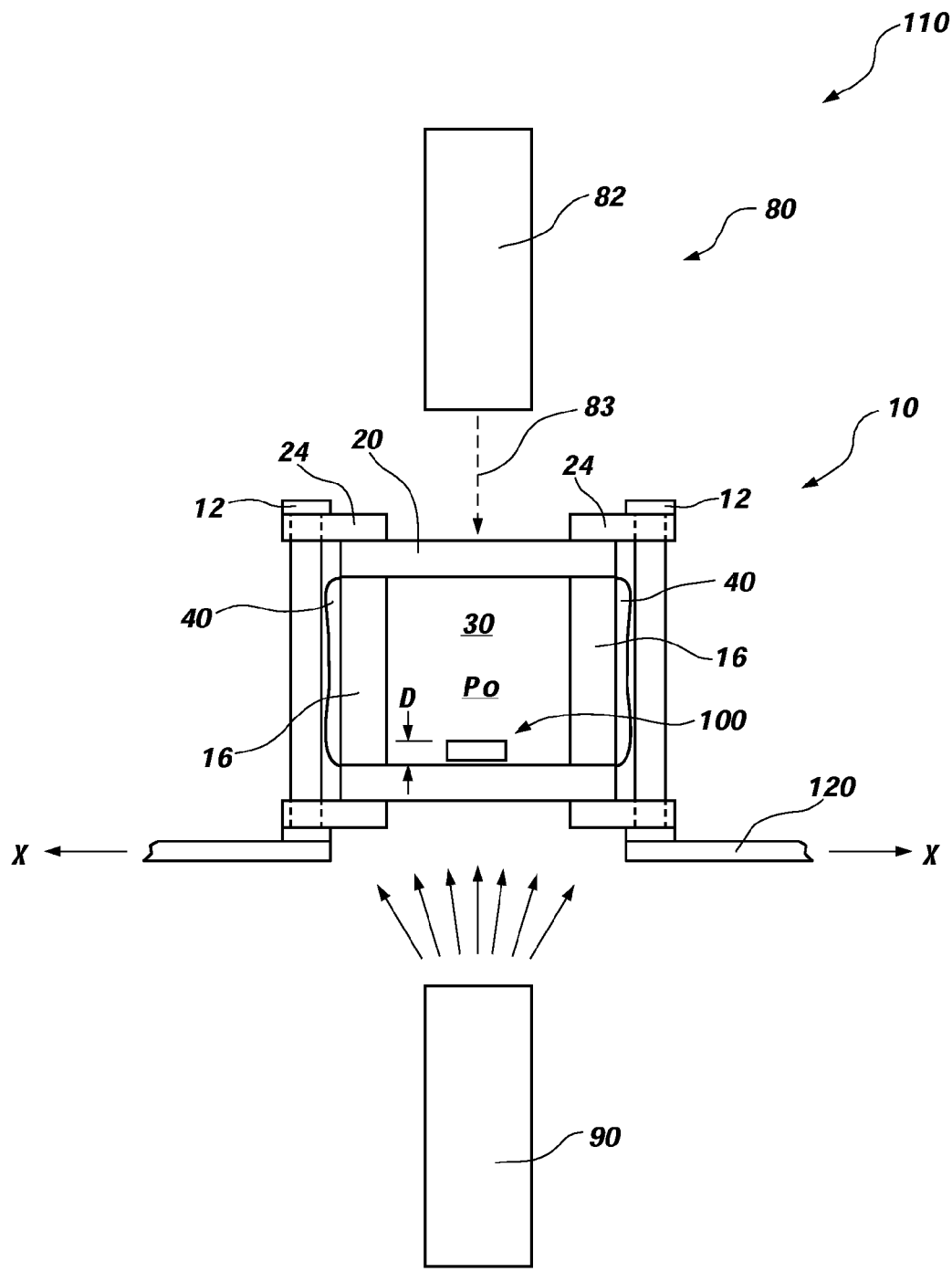
FIG. 2A shows a schematic side cross-sectional view of an exemplary dimensional measurement apparatus in accordance with the present invention.

A process for measurement of a dimensional characteristic of a sample according to the present invention will be described with reference to FIGS. 2A-2B. FIG. 2A shows a schematic side cross-sectional view of a dimensional measurement apparatus 110 in accordance with the present invention. Dimensional measurement apparatus 110 may include pressure vessel 10, optical perception device 80, and light emitting device 90. In particular, optical perception device 80 may be positioned proximately above and oriented substantially perpendicular to upper window 20 and light emitting device 90 may be positioned proximately below and oriented to direct light emitted therefrom toward lower window 22. Of course, such a configuration may cause light emitted from light emitting device 90 to pass into and through chamber 30, and toward optical perception device 80. Thus, such a configuration may facilitate optical perception of a sample 100 disposed within chamber 30.

Light emitting device 90 may comprise one or more incandescent or fluorescent light, as known in the art, without limitation. Further, while light emitting device 90 is shown as being positioned proximately below and oriented to direct light emitted therefrom toward lower window 22, many alternative configurations are contemplated by the present invention. For instance, light emitting device 90 may be placed within chamber 30, if light emitting device 90 is capable of resisting damage due to pressure developed therein. Alternatively, light emitting device 90 may be positioned above upper window 20 and may be oriented to direct light emitted therefrom toward upper window 20.

It may be appreciated that optical perception of sample 100 within chamber 30 may not require at least one window forming at least a portion of pressure vessel 10. Rather, perception of sample 100 may occur via fiber optic techniques or the like. Similarly, light may be introduced into chamber 30 via fiber optic techniques or as otherwise known in the art. Therefore, more generally, chamber 30 may include apparatus for optical perception of an object disposed therein, without limitation.

For instance, optical perception device 80 may comprise a microscope. For instance, optical perception device 80 may comprise a filar digital microscope. A filar digital microscope may include movement mechanisms such as so-called linear bearings, rails, slides, or pillow block bearings, precision lead screws or other movement mechanisms may be configured for moving movable stage 120 carrying pressure vessel 10 along axes X and Y manually or via a motor, as known in the art. Of course, corresponding distance indicators for indicating relative motion of movable stage 120 along axes X and Y may be used. In more detail, axes X and Y define a geometrical plane in which the movable stage 120 may move relative to the viewable indicium 88. Preferably, the line of sight 83 of viewing aperture 82 may be oriented substantially perpendicular to the geometrical plane defined by axes X and Y. Such a configuration may reduce errors in a measurement of at least one dimension of sample 100.

Also, viewing aperture 82 may include indicium 88 (FIG. 2B) for facilitating measurement, shown as a cross-hair or two substantially perpendicular axes, of an object viewed therethrough, as known in the art. Such measurement microscopes may be commercially available from Gaertner Scientific, of Skokie, Ill. Of course, indicium 88 is merely shown for completeness and clarity. It should be understood that indicium 88 is viewable through viewing aperture 82 as a superimposed image that may be useful in determining relative measurement of an object viewed therethrough. Further, indicium 88 may comprise more than one mark or symbol, thus, indicium 88 may comprise indicia, without limitation.

Typically, a microscope which is configured for measuring objects viewed therethrough may include a movable stage 120 for moving the object that is viewed therewith in relation to the viewing aperture 82. However, the present invention contemplates that the viewing aperture 82 may be movable in relation to sample 100 or, alternatively, sample 100 may be movable in relation to the viewing aperture 82 of the optical perception device 80, without limitation. Likewise, the sample 100 to be measured may move in relation to light emitting device 90, or vice-versa, without limitation. It may be preferable, however, to orient the viewing aperture 82 and the light emitting device 90 generally toward one another. Such a configuration may facilitate measurement of sample 100, as described in greater detail hereinbelow.

During operation, a first or "initial" measurement of a dimension of sample 100 may be performed. More specifically, the initial length and width of sample 100 may be measured. Generally, length, as used herein, of sample 100 refers to a dimension of sample 100 in a direction Y as shown in FIG. 2B. Additionally, width, as used herein, of sample 100 refers to a dimension thereof in a direction X as shown in FIG. 2B.

Of course, the environment within chamber 30 may be adjusted or controlled. For example, the environment within the chamber 30 may be initially controlled by flushing chamber 30 with a desired fluid in the form of a gas or liquid. Further, one or more of the temperature, gas environment, and pressure $P_0$ within chamber 30 may be selected and controlled in relation to initial disposition and measurement of one or more dimensions of sample 100.

Figure 2B:
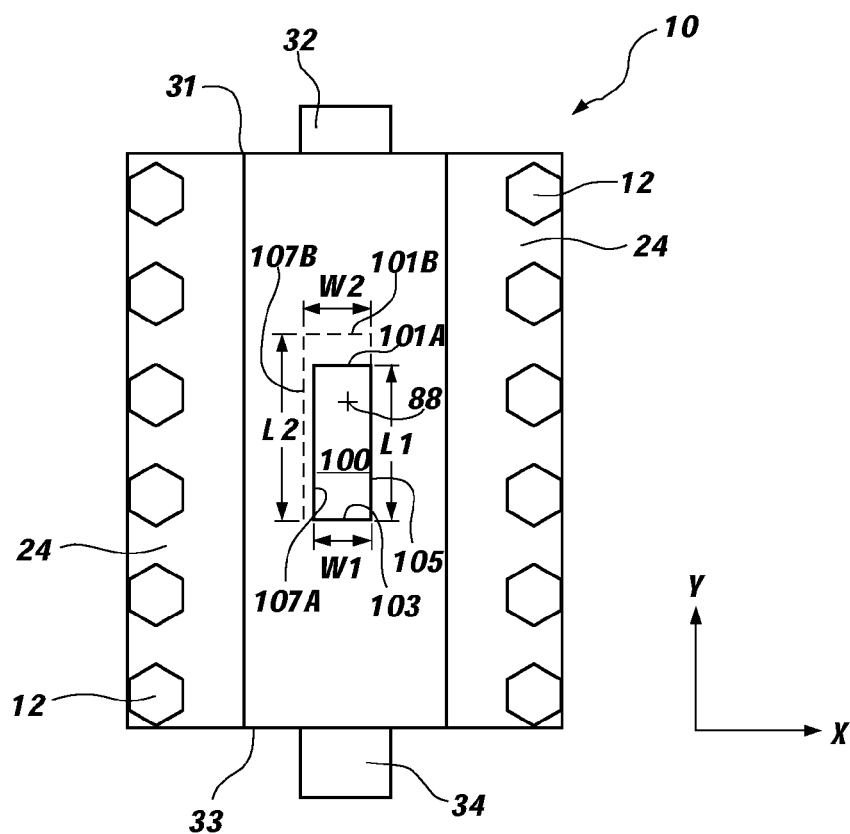
FIG. 2B shows a top elevation view of the dimensional measurement apparatus shown in FIG. 2A.

For instance, referring to FIG. 2B, an initial length, labeled "L1" may be measured by visually aligning an indicia (not shown) viewable through the viewing aperture 82 with edge 103, moving sample 100 relative to indicium 88 (i.e., the viewing aperture 82) so as to visually align indicium 88 with edge 101A, and indicating the magnitude or amount of relative travel. Similarly, an initial width, labeled "W1" may be measured by visually aligning an indicium 88 viewable through the viewing aperture 82 with edge 105, moving sample 100 relative to indicium 88 so as to visually align indicium 88 with edge 107A, and indicating the magnitude of relative travel.

Alternatively, the size of sample 100 may be known prior to disposal within chamber 30, by way of conventional measurement techniques as known in the art. For instance, a micrometer may be used to determine a magnitude of at least one dimension of a sample 100 prior to disposition within chamber 30.

When disposed within chamber 30, the position of sample 100 may be fixed in relation to pressure vessel 10. Fixing the position of one or both of edges 103 and 105 may allow for ease in measurement of one or both of the length or width, correspondingly, of sample 100. That is, put another way, fixing the position of one or both of edges 103 and 105 may substantially eliminate the need to repeat determination of the position of one or both of edges 103 and 105. Put another way, the position of one or both of edges 103 and 105 may be "zeroed," initially, so that the "free" edge or edges of the sample 100 may be subsequently measured or determined in relationship to its other corresponding fixed edge, respectively, without additionally determining the position thereof.

Although sample 100 is shown as being generally rectangular as it is oriented for measurement and shown in a top elevation view in FIG. 2B, there are many potential shapes and sizes that sample 100 may exhibit. Generally, sample 100 may comprise circular, cylindrical, or irregular shapes. It may be preferable for sample 100 to exhibit a discernible edge feature, however, for ease and consistency in visual alignment of indicium 88 therewith.

Subsequent to an initial measurement of sample 100, an environmental characteristic within chamber 30 may be altered. Particularly, the pressure $P_0$ within chamber 30 may be changed by introduction of gas into chamber 30 through port 32 or by elimination of gas from chamber 30 through port 34, or vice versa. For instance, the magnitude of pressure $P_0$ within chamber 30 may be increased. In response to the increase in pressure, the dimensions of sample 100 may subsequently increase. Alternatively, it may be desired to reduce pressure $P_0$ within chamber 30 by removing a quantity of gas via port 32 or port 34.

Subsequent to the change in an environmental condition within chamber 30, at least a second width measurement, labeled "W2" may be measured by visually aligning indicium 88 of the viewing aperture 82 with edge 105, moving sample 100 relative to the indicia (i.e., the viewing aperture 82) so as to visually align the indicia with edge 107B, and indicating the magnitude of the relative travel. Similarly, a second length measurement, labeled "L2" may be measured by visually aligning indicium 88 of the viewing aperture 82 with edge 103, moving sample 100 relative to the indicia (i.e., the viewing aperture 82) so as to visually align the indicia with edge 100B, thus indicating the magnitude of the relative travel and, distance L2.

It may be advantageous to measure more than one dimension of a sample 100 because the dimensional change thereof may be anisotropic. Put another way, it may be advantageous to measure more than one dimension of a sample 100 to determine the relative magnitude of anisotropy of a sample 100. For instance, one or more of length, width, or depth (labeled "D" in FIG. 2A) of a sample 100 may be measured by way of the dimensional measurement apparatus 110, without limitation. It may be appreciated that additional windows (not shown) may be added to pressure vessel 10 to facilitate measurement of the depth "D" of sample 100.

In one particular example, sample 100 may comprise a coal sample and the gas within the chamber may comprise carbon dioxide. Thus, the sample 100 may adsorb carbon dioxide and may expand in response thereto. Further, such dimensional expansion may be a function of the pressure of the carbon dioxide. By measuring the changes in dimension of a coal sample in relation to different pressures of gas, the relationship between the dimensional behavior (expansion or contraction) of coal and the pressures under which such behavior occurs may be determined.

Further, as used herein, the term "adsorption" (as well as its various forms) may include the meanings of either or both of the terms "adsorption" as well as "absorption." Put another way, the meaning of "adsorption," as used herein, may be interchangeable with or inclusive of the term "absorption," depending on the mechanism by which a constituent is taken into or within a sample. Of course, the mechanism or mechanisms by which a constituent is taken into or within a sample may depend upon the composition of both the sample and the constituent.

Further, it should be readily appreciated that the present invention is not limited in relating to materials which adsorb a gas. Rather, sample 100 may generally comprise any material which expands or contracts in response to an environmental change. For instance, shale, sandstone, or hydrophilic materials may comprise sample 100. Additionally, expansion or contraction of a sample 100 may occur by way of any mechanism or in response to any environmental condition as known in the art, without limitation.

Regarding coal, dimensional behavior thereof, once obtained, may be useful in developing mathematical modeling of injection of carbon dioxide or another gas or liquid into a coal bed, because expansion or contraction of coal may affect the permeability thereof. Inclusion or consideration of dimensional changes of coal with respect to permeability thereof may improve the accuracy of modeling or simulating the injection of carbon dioxide into coal. In turn, improved accuracy in modeling of the injection of carbon dioxide into coal may increase the effectiveness or efficiency with which carbon dioxide may be injected into coal for stimulation of methane production or for carbon dioxide sequestration. More generally, the present invention contemplates that the relationship between a gas and the pressure thereof and the dimensional behavior of a permeable sample may be determined.

In another aspect of the present invention, adsorption or desorption of a gas by a permeable sample is a process which may continue during a relatively long amount of time. For instance, coal samples which are inches in length, width, and height may take months to equilibrate when exposed to a selected pressure of carbon dioxide.

Accordingly, it may be desirable to ascertain, subsequent to a change in a condition within chamber 30, whether the dimensional response of the sample 100 has substantially reached equilibrium. Equilibrium, as used herein, means that a dimension which is changing in response to a change in environment is within about 95% or more of its maximum value. Put another way, it may be desirable to wait, after a change in environment, until the rate of change in volume of sample 100 is relatively small or zero. Such a determination may be accomplished by aligning the indicium 88 of the viewing aperture 82 with a free edge of the sample 100 and observing, during a predetermined amount of time, whether the observed free edge changes position and if so, evaluating the magnitude of the change in position. However, equilibrium with respect to the relative rate of dimensional change of sample 100 may be relative, and may vary in relation to the material comprising sample 100 as well as the selected testing conditions within chamber 30.

In this regard, it may preferable to limit the volume of a sample to reduce or limit the amount of time needed to reach equilibrium. Also, limiting the size of a sample may be necessary for disposition within the chamber 30, depending on the relative size of port 32 or port 34, respectively. More specifically, the present invention contemplates that samples having an initial volume, at roughly ambient atmospheric pressure and a temperature of about 70° Fahrenheit, of less than about 1 in$^3$ may be useful for determining the dimensional behavior thereof responsive to exposure to a selected gas at a selected magnitude of pressure. For example, a sample may be about 1 inches long, 0.25 inches in width, and 0.25 inches in height. Limiting the size of a sample for use in the dimensional measurement apparatus of the present invention may reduce the amount of time required for reaching equilibrium via adsorption and desorption or may reduce the amount of time needed for estimating a future equilibrium state, as discussed in further detail hereinbelow.

In a further aspect of the present invention, it may be possible to estimate the amount of change in a dimension of a sample prior to allowing the sample to substantially equilibrate. More particularly, it has been discovered by the inventors hereof that the relationship between a change in a dimension of a coal sample and time may be approximated by:

$$S(t) = \frac{S_{FINAL}(\Delta p) \cdot t}{T + t} \quad \text{Equation 1}$$

where:

S(t) is a measured change in a dimension (at time t) divided by the initial dimension;

$S_{FINAL}(\Delta P)$ is the maximum change in a dimension for a given change in pressure divided by the initial dimension (if t extends to a long time);

t is an elapsed time after a change in a pressure; and

T is a constant which equals the amount of time corresponding to when S(t) equals one-half of $S_{FINAL}$.

Accordingly, the constant T may be obtained by changing the pressure within chamber 30, and monitoring one or more dimensions of the sample 100 in response thereto for a relatively long time. The data may be collected and may be "fit" to the above-referenced equation and constants T and $S_{FINAL}(\Delta P)$ chosen so as to minimize the deviation between the actual data and the equation. Put another way, T and $S_{FINAL}(\Delta P)$ may be selected to provide the "best fit" to the actual, empirical data collected.

Assuming that T is constant over a range of pressures, after T is determined by the process discussed above, the maximum amount of change in a dimension of the sample in response to another subsequent change in pressure may be estimated or predicted prior to the sample reaching equilibrium. More specifically, one or more measurements of a dimension at one or more respective times (i.e., elapsed time from the change in pressure) may be used to calculate $S_{FINAL}$ by substitution into an equation of the form:

$$S_{FINAL}(\Delta P) = \frac{S(t) \cdot (T+t)}{t}. \qquad \text{Equation 2}$$

Thus, a plurality of measurements (S(t)) at respective times t may be used to compute predicted values of $S_{FINAL}$(ΔP). Of course, the plurality of predicted $S_{FINAL}$(ΔP) (each corresponding to different time t) may be averaged or otherwise mathematically combined to calculate a predicted value of $S_{FINAL}$(ΔP). Of course, once $S_{FINAL}$(ΔP) is predicted with a desired level of confidence, it may be desirable to increase the pressure additionally, so as to acquire another data point and reduce the overall time required to complete the testing.

Of course, additional changes in pressure may be analyzed in the same way, by predicting or estimating $S_{FINAL}$ prior to the sample reaching equilibrium. However, changing the pressure before a sample has reached equilibrium with respect to a previous pressure change may present some difficulty. For instance, presumably, the sample would continue to expand in response to a previous change in pressure until reaching $S_{FINAL}$(ΔP) associated therewith.

Therefore, Equation 1 may be used to continue to predict the amount of dimensional change that would occur due to a previous change in pressure and that amount of dimensional change may be subtracted from the measured change in dimension prior to application of Equation 2. Put another way, changes in dimension due to a previous pressure change may be predicted and corrected (subtracted from) changes in dimension measured after a subsequent change in pressure.

Illustratively, the overall change in dimension of a sample with respect to a plurality of pressure changes may be conceptually and mathematically contemplated as a summation of a series of respective Equation 1 functions, after $S_{FINAL}$(ΔP) has been calculated as shown below:

$$S(t) = S(\Delta P)_1 + S(\Delta P)_2 + S(\Delta P)_3 \qquad \text{Equation 3}$$

Where:
S(ΔP)$_1$ is a predicted change in a dimension of a sample with respect to a first change in pressure;
S(ΔP)$_2$ is a predicted change in a dimension of a sample with respect to a second change in pressure;
S(ΔP)$_3$ is a predicted change in a dimension of a sample with respect to a third change in pressure.

Or, in another form:

$$S(t) = \sum_N S(\Delta P)_n \qquad \text{Equation 4}$$

Where S(ΔP)$_n$ is a predicted change in a dimension of a sample with respect to an nth change in pressure; and
N is the total number of changes in pressure.

Considering the hypothetical situation where one pressure change has occurred, Equation 1 may be used to predict the amount of dimensional change forward in time as a function thereof. Therefore, after another pressure change occurs, the predicted change in dimension that may continue to occur due to the first pressure change may be subtracted from measured values, so as to isolate the dimensional change that results in response to the subsequent pressure change.

$$S(t)_{CORRECTED} = S(t)\text{measured} - [S(\Delta P)_1 + S(\Delta P)_2 \ldots] \qquad \text{Equation 5}$$

Then, the corrected measurements corresponding to the subsequent pressure change may be used to predict $S_{FINAL}$(ΔP) corresponding to the subsequent pressure change via Equation 2. This process may be repeated for any number of pressure changes, assuming T is constant. As more pressure changes occur, previous dimensional effects associated therewith may be corrected by application of Equation 5. However, it may be appreciated that these effects may be relatively small in relation to the effects of a subsequent (more temporally proximate) change in pressure. Therefore, optionally, once a change in dimension relating to a previous pressure change is relatively minimal with respect to a change in dimension associated with at least one more recent pressure change it may be determined that such a correction is insignificant and thus, may be ignored.

Thus, once T has been determined, assuming that T is constant, depending on the size of the sample, $S_{FINAL}$(ΔP) may be predicted with relative accuracy within about 24 hours from the change in pressure. Such a configuration may accelerate testing processes for determining dimensional changes in coal as a function of exposure to a selected gas at a selected pressure.

Thus, generally, the present invention contemplates that a sample may be placed within a chamber, a characteristic of the environment within the chamber altered, and a change in dimension of the sample measured in response thereto. The discussion above relates generally to a change in pressure within chamber 30; however, other environmental conditions may be changed within chamber 30, without limitation. For instance, temperature, humidity, or the gas or liquid or constituency of the gas or liquid (such as relative concentrations of the constituents thereof) surrounding sample 100 may be altered within chamber 30.

In addition, at least one measurement of a change in dimension of sample 100 may be performed at each of a plurality of different magnitudes of pressures. Put another way, data may be collected that relates pressure to a measurement of a change in dimension of sample 100. More generally, an environmental condition within the chamber 30 of the dimensional measurement apparatus 110 may be altered, and at least one measurement prior to the alteration of the condition and at least one measurement subsequent to the alteration of the condition may be obtained for determining the change in dimension corresponding to the change in environmental condition. The process may be repeated so as to collect data that reflects a magnitude of change in dimension of a sample to a respective change in an environmental condition.

In another aspect of the present invention, a plurality of samples may be placed within chamber 30 and at least one dimension of each of the plurality of samples may be optically measured in response to a change in a characteristic of the environment of chamber 30.

Figure 3A:
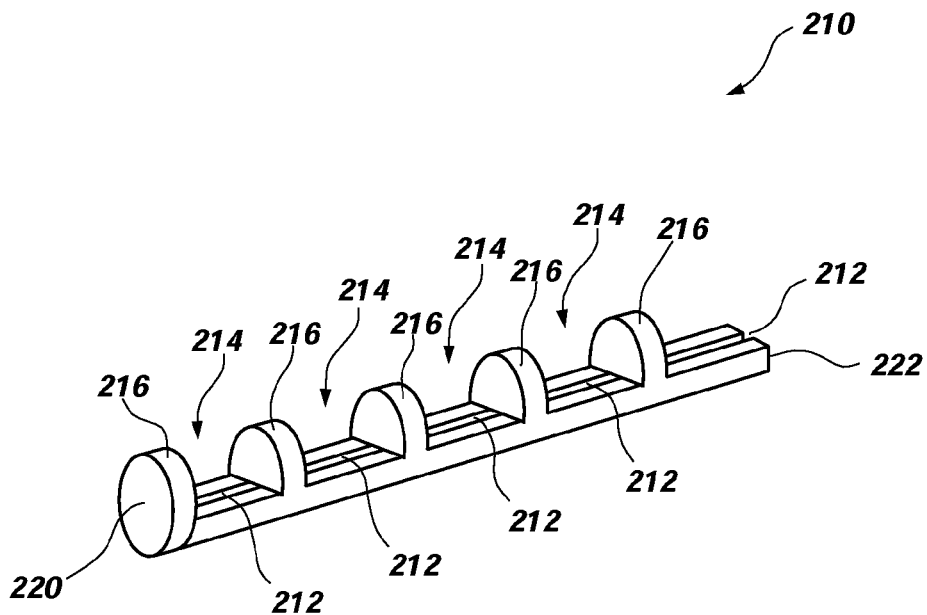
FIG. 3A shows a perspective view of an exemplary sample holder in accordance with the present invention.
Figure 3B:
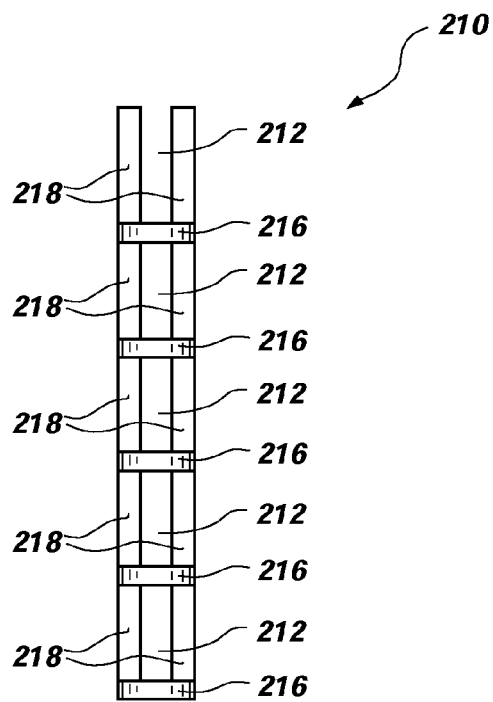
FIG. 3B is a top elevation view of the sample holder shown in FIG. 3A.

FIG. 3A shows a perspective view of a sample holder 210 according to the present invention including a plurality of recesses 214 formed within its body, separated therealong between lower end 220 and upper end 222 by spaced-apart flanges 216. Also, as illustrated in FIG. 3B, which shows a top elevation view of sample holder 210, apertures 212 may be formed between side members 218 of each recess 214. Apertures 212 may facilitate visual measurement of a sample disposed within one of recesses 214, as described hereinbelow.

Figure 3C:
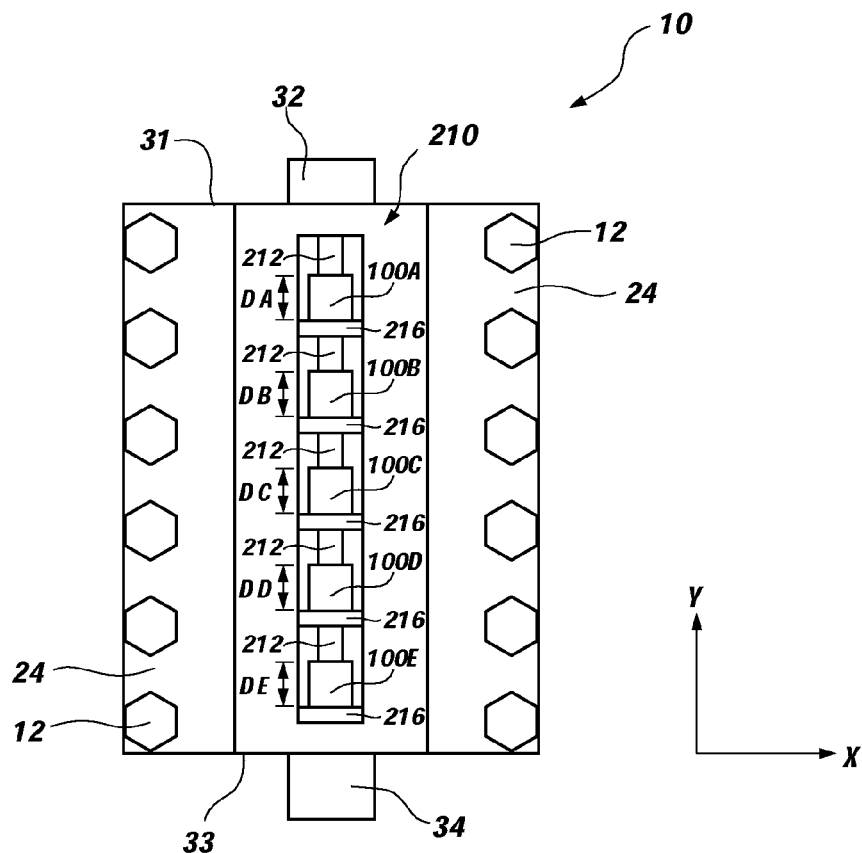
FIG. 3C is a top elevation view of the dimensional measurement apparatus shown in FIG. 2A including the sample holder shown in FIGS. 3A and 3B.

For instance, FIG. 3C shows a top elevation view of sample holder 210 disposed within the chamber of pressure vessel 10, as it may be viewed through window 20. The position of sample holder 210 within pressure vessel 10 may be fixed with respect to pressure vessel 10. Such a configuration may facilitate measurements of one or more dimensions of each of samples 100A, 100B, 100C, 100D, and 100E. Each of samples 100A, 100B, 100C, 100D, and 100E may be disposed within one of recesses 214 of sample holder 210, respectively. Measurements may be obtained by direct measurement of one or more dimensions of each of 100A, 100B, 100C, 100D, and 100E as explained above in relation to dimensional measurement apparatus 110 as shown in FIGS. 2A and 2B.

Alternatively, if pressure vessel 10, as shown in FIG. 3C is configured within a dimensional measurement apparatus similar to the dimensional measurement apparatus 110 shown in FIG. 2A, light emitting device 90 may illuminate the portion of each of apertures 212 that is not blocked by a respective sample 100A, 100B, 100C, 100D, or 100E. Further, measuring the portion of apertures 212 which are visible through window 20 and may be useful for determining a dimension of each of samples 100A, 100B, 100C, 100D, and 100E implicitly (i.e., by comparison of the overall size of an aperture 212 to the portion thereof that is not blocked by a respective sample). Thus, distances DA, DB, DC, DD, and DE may be obtained by measurement or perception of the portion of each of apertures 212 that is not blocked by a respective sample 100A, 100B, 100C, 100D, or 100E. Further, each of samples 100A, 100B, 100C, 100D, and 100E may abut against a respective surface of each of spaced-apart flanges 216 or, optionally, may be affixed to the sample holder so as to remain abutted thereagainst.

It should be noted that the process for visual measurement of at least one dimension of a sample disposed within a pressure vessel may be automated. For instance, an imaging device, such as, for instance, a digital camera may be used to capture an image of one or more samples disposed within chamber 30 of pressure vessel 10. Then, a computer program may be utilized to analyze the image to determine a dimension of the one or more samples disposed within chamber 30 of pressure vessel 10. Of course, computer programs and data acquisition and control hardware may be utilized to automate measurement of a dimension of a sample disposed within a chamber 30 of pressure vessel 10, changing an environmental condition therein, or both. Such a configuration may improve the ease with which samples may be analyzed.

Figure 3D:
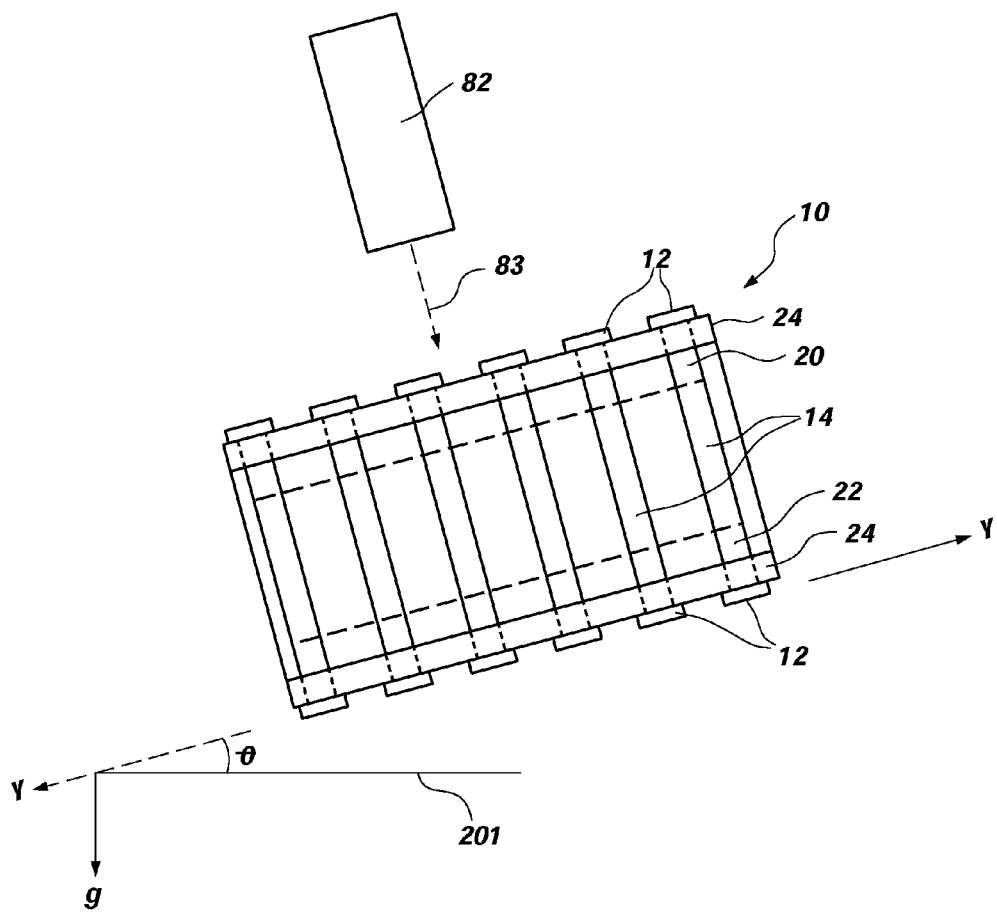
FIG. 3D is a side schematic view of the dimensional measurement apparatus shown in FIG. 3C oriented at an angle with respect to a horizontal axis.

In yet a further aspect of the present invention, the pressure vessel 10 may be inclined at an angle with respect to the horizontal axis. For example, FIG. 3D shows a pressure vessel 10 which is inclined at an angle θ with respect to the horizontal axis 201. Movable stage 120 is not shown in FIG. 3D, for clarity, but may be present as shown in FIG. 2A. Orienting the pressure vessel 10 at an angle with respect to the horizontal axis may be advantageous in that a gravitational force of sufficient magnitude (i.e., due to the earth's gravitational field) may cause each of samples 100A, 100B, 100C, 100D, and 100E to abut against a respective surface of each of spaced-apart flanges 216. Thus, during expansion of any of samples 100A, 100B, 100C, 100D, or 100E, any thereof may remain abutted against each of spaced-apart flanges 216, respectively.

More particularly, as shown in FIG. 3D, a direction of an earthly gravitational force, labeled "g," may not be substantially perpendicular to a geometrical plane defined by axes X (FIGS. 2A and 2B) and Y in which the measurement is to be taken. Orienting the geometrical plane of measurement substantially nonperpendicularly in relation to an earthly gravitational force may be advantageous for causing samples 100A, 100B, 100C, 100D, or 100E, to remain abutted against each of spaced-apart flanges 216, respectively.

Figure 4:
FIG. 4 depicts a method of simulating injection of a gas into a subterranean formation comprising coal.
Figure 4:

In addition to improvement of testing methods and apparatus for optical measurement of dimensional changes in samples in response to selected chamber conditions, the experimental data obtained may be otherwise useful. Particularly, FIG. 4 depicts a method of simulating injection of a selected gas into a subterranean formation comprising a coal composition. As explained in detail hereinabove, in accordance with the present invention, optical measurement of dimensional changes of a given coal composition as a function of exposure to a selected gas over a range of pressure may be performed. Further, dimensional changes of a particular coal composition over the range of pressure of a selected gas may be related, as known in the art, to a permeability characteristic thereof. Such permeability relationship may be used in simulating injection of a selected gas into a subterranean formation including a particular coal composition.

Of course, such simulation may be repeated and the conditions of the simulated injection may be varied so as to optimize a particular objective. Particularly, simulation may be repeated and the conditions of the simulated injection may be varied so as to optimize adsorption of the gas injected. For instance, methane production via injection of a selected gas may be modeled and the injection simulation may be repeated for optimizing methane production. Similarly, sequestration of a selected gas may be modeled and the injection simulation may be repeated for optimizing thereof. Of course, ultimately, a selected gas may be injected into a subterranean formation including the coal composition according to the determined simulation conditions that optimize the simulated adsorption of the selected gas.

While the present invention has been described herein with respect to certain preferred embodiments, those of ordinary skill in the art will recognize and appreciate that it is not so limited. Rather, many additions, deletions and modifications to the preferred embodiments may be made without departing from the scope of the invention as hereinafter claimed. In addition, features from one embodiment may be combined with features of another embodiment while still being encompassed within the scope of the invention. Therefore, the invention is to encompass all modifications, equivalents, and alternatives falling within the spirit and scope of the invention as defined by the following appended claims.

What is claimed is:

1. A method of simulating injection of a gas into a subterranean formation, the method comprising:
    optically measuring at least one dimensional change of a sample of selected composition as a function of exposure to a selected gas for at least a first pressure and a second differing pressure;
    relating the optically measured at least one dimensional change of the sample of selected composition to a permeability characteristic thereof; and
    simulating injection of the selected gas into a subterranean formation including the selected composition.

2. The method of claim 1, further comprising:
    repeating simulating injection of the selected gas into the subterranean formation including the selected composition under a plurality of differing simulation conditions; and determining simulation conditions that optimize at least one of a simulated adsorption and a simulated desorption of the selected gas.

3. The method of claim 1, wherein the selected subterranean formation comprises coal and further comprising:

repeating simulating injection of the selected gas into the subterranean formation including the selected composition under a plurality of differing simulation conditions; and determining simulation conditions that optimize a simulated production of methane from the subterranean formation.

4. A method of injecting gas into a subterranean formation, the method comprising:

optically measuring at least one dimensional change of a sample of selected composition as a function of exposure to a selected gas for at least a first pressure and a second differing pressure;

relating the optically measured at least one dimensional change of the sample of selected composition to a permeability characteristic thereof;

simulating injection of the selected gas into a subterranean formation including the selected composition;

determining simulation conditions that optimize a simulated adsorption of the selected gas; and injecting the selected gas into a subterranean formation including the selected composition substantially according to the determined simulation conditions that optimize the simulated adsorption of the selected gas.

5. A method of producing methane from a subterranean formation, the method comprising:

optically measuring at least one dimensional change of a sample of a coal composition as a function of exposure to a carbon dioxide gas for at least a first pressure and a second differing pressure;

relating the optically measured at least one dimensional change of the sample of the coal composition to a permeability characteristic thereof;

simulating injection of the carbon dioxide gas into a subterranean formation including the coal composition;

simulating a production of methane from the subterranean formation in response to the simulated injection of carbon dioxide gas;

determining simulation conditions that optimize the simulated production of methane; and injecting carbon dioxide into the subterranean formation including the coal composition substantially according to the determined simulation conditions that optimize the simulated production of methane.

* * * * *